(12) United States Patent
Kim et al.

(10) Patent No.: US 8,529,458 B2
(45) Date of Patent: Sep. 10, 2013

(54) METHOD AND APPARATUS FOR ASSESSMENT OF FLUID RESPONSIVENESS

(75) Inventors: Sunghan Kim, Los Angeles, CA (US); Pedro Mateo Riobo Aboy, Portland, OR (US); James McNames, Portland, OR (US)

(73) Assignees: State of Oregon by and Through the State Board of Higher Education on Behalf of Portland State University, Portland, OR (US); APDM, Inc., Portland, OR (US)

( * ) Notice: Subject to any disclaimer, the term of this patent is extended or adjusted under 35 U.S.C. 154(b) by 321 days.

(21) Appl. No.: 12/891,795

(22) Filed: Sep. 27, 2010

(65) Prior Publication Data

US 2011/0077532 A1   Mar. 31, 2011

Related U.S. Application Data

(60) Provisional application No. 61/246,454, filed on Sep. 28, 2009, provisional application No. 61/246,456, filed on Sep. 28, 2009.

(51) Int. Cl.
*A61B 5/02* (2006.01)

(52) U.S. Cl.
USPC ........... 600/485; 600/486; 600/487; 600/500; 600/504

(58) Field of Classification Search
USPC .................. 600/485–487, 500, 504
See application file for complete search history.

(56) References Cited

U.S. PATENT DOCUMENTS

| | | |
|---|---|---|
| 6,776,764 B2 | 8/2004 | Pinsky |
| 7,225,013 B2 | 5/2007 | Amir |
| 7,422,562 B2 | 9/2008 | Hatlib |
| 2009/0069647 A1 | 3/2009 | McNames |

OTHER PUBLICATIONS

McNames et al., Statistical Modeling of Cardiovascular Signals and Parameter Estimation Based on the Extended Kalman Filter, IEEE Transactions on Biomedical Engineering, vol. 55, No. 1, Jan. 2008, pp. 119-129.*
Djurić et al. "Particle filtering," IEEE Signal Process. Mag., vol. 20, No. 5, pp. 19-38, Sep. 2003.*
Wikipedia reference on Kalman Filter relationship to Bayesian estimator.*
McNames J; Aboy M; "Cardiovascular Signal Decomposition and Estimation with the Extended Kalman Smoother", EMBS Annual International Conference, Aug. 30-Sep. 3, 2006.

* cited by examiner

*Primary Examiner* — Michael Kahelin
*Assistant Examiner* — Tho Tran
(74) *Attorney, Agent, or Firm* — Mateo Aboy; Aboy&Associates PC (57) ABSTRACT

Methods and apparatus for determining a cardiac parameter from cardiovascular pressure signals including arterial blood pressure (ABP) and the photoplethysmographic signal to quantify the degree of amplitude modulation due to respiration and predict fluid responsiveness are disclosed. Disclosed embodiments include a method for assessing fluid responsiveness implemented in a digital computer with one or more processors comprising: (a) measuring a cardiovascular signal, and (b) computing a dynamic index predictive of fluid responsiveness from said cardiovascular signal using a nonlinear state space estimator. According to one particular embodiment, and without limitation, the nonlinear state space estimator is based on a model for cardiovascular signals such as arterial blood pressure or plethysmogram signals, and employs a marginalized particle filter to estimate a dynamic index predictive of fluid responsiveness that is substantially equivalent to a variation in pulse pressure of said cardiovascular signal.

18 Claims, 7 Drawing Sheets

METHOD AND APPARATUS FOR ASSESSMENT OF FLUID RESPONSIVENESS

CROSS-REFERENCE TO RELATED APPLICATIONS

This application claims the benefit of U.S. Provisional Application No. 61/246,454 and U.S. Provisional Application No. 61/246,456 both filed on 2009-09-28 by the present inventors, which are incorporated herein by reference.

TECHNICAL FIELD

Disclosed embodiments relate to methods and apparatuses for cardiac monitoring. Specifically, they relate to methods and apparatuses for to dynamic estimation of fluid responsiveness.

BACKGROUND

Indicators and methods for noninvasive determination of fluid status of patients are important for monitoring of the condition of critical care patients. In many critical care settings clinicians must decide whether patients should be given intravenous fluid boluses and other therapies to improve perfusion. Excessive fluid can be damaging by impairing lung function when it decreases oxygen delivery to tissues and contributes to organ failure. Insufficient fluid can result in insufficient tissue perfusion which can also contribute to organ failure. Determining the best course of fluid therapy for a given patient is difficult and clinicians have few clinical signs to guide them.

Fluid administration in hemodynamically unstable patients is often a major challenge when it-comes to measuring stroke volume (SV), cardiac output (CO), or other hemodynamic parameters in real time. Correct clinical assessment of hypovolemia is difficult, as is the decision to undertake fluid resuscitation as the initial treatment strategy. Specifically, it is very difficult to predict whether a hemodynamically unstable patient will respond to fluid therapy with an increase in stroke volume and cardiac output. Moreover, fluid overload can cause significant pulmonary or cardiac dysfunction, whereas fluid insufficiency may cause tissue damage resulting in vital organ dysfunction. A patient's fluid responsiveness is the major and most important determinant to assess the adequacy of fluid resuscitation therapy and to ensure optimal cardiac performance and organ perfusion.

There are several dynamic parameters that can be used to assess fluid responsiveness from arterial blood pressure (ABP) and in some cases from plethysmogram signals. Several bedside indicators of ventricular preload have been used as predictors of fluid responsiveness. Right arterial pressure (RAP) and pulmonary artery occlusion pressure (PAOP) are commonly used in the intensive care unit (ICU) when deciding to administer fluids. Other bedside indicators of ventricular preload include right ventricular end diastolic volume (RVEDV) and left ventricular end diastolic area (LVEDA) measured with transesophageal echocardiography. Several studies and case reports have shown, however, that these static indicators based on cardiac filling pressures many have poor predictive value and often fail to give adequate information about fluid responsiveness.

Several studies have confirmed the clinical significance of monitoring the variations observed in left ventricular stroke volume that result from the interaction of the cardiovascular system and the lungs under mechanical ventilation. These stroke volume variations (SVV) are caused by the cyclic increases and decreases in the intrathoracic pressure due to the mechanical ventilation, which lead to variations in the cardiac preload and afterload. SVV has recently been extensively investigated and several studies have shown the usefulness of using SVV as predictor of fluid responsiveness in various clinical situations. Several other parameters based on SVV have been found to be useful as well. In particular, systolic pressure variation (SPV) with its delta-Up and delta-Down components has been found to be a very useful predictor of fluid responsiveness. SPV is based on the changes in the arterial pulse pressure due to respiration-induced variations in stroke volume. Yet another parameter that has recently been investigated and shown to be a valid indicator of fluid responsiveness is the pulse pressure variation (PPV).

The pulse pressure variation (PPV) index is a measure of the respiratory effect on the variation of systemic arterial blood pressure in patients receiving full mechanical ventilation. It is a dynamic predictor of increases in cardiac output due to an infusion of fluid. Numerous studies have demonstrated that PPV is one of the most sensitive and specific predictors of fluid responsiveness. Specifically, PPV has been shown to be useful as a dynamic indicator to guide fluid therapy in different patient populations receiving mechanical ventilation. For instance, PPV was found to exhibit better performance as a predictor of fluid responsiveness in patients before off-pump coronary artery bypass grafting than standard static pre-load indices. PPV has also been shown to be useful for predicting and assessing the hemodynamic effects of volume expansion and a reliable predictor of fluid responsiveness in mechanically ventilated patients with acute circulatory failure related to sepsis.

The standard method for calculating PPV often requires simultaneous recording of arterial and airway pressure. Pulse pressure (PP) is manually calculated on a beat-to-beat basis as the difference between systolic and diastolic arterial pressure. Maximal PP ($PP_{max}$) and minimal PP ($PP_{min}$) are calculated over a single respiratory cycle, which is determined from the airway pressure signal. Pulse pressure variations PPV are calculated in terms of $PP_{max}$ and $PP_{min}$, and expressed as a percentage, $$PPV(\%) = 100 \times \frac{PP_{max} - PP_{min}}{(PP_{max} + PP_{min})/2} \qquad (1)$$

There are few available methods or apparatuses to automatically estimate PPV accurately and reliably. A limitation of current PPV methods is that they do not work adequately in regions of abrupt hemodynamic changes and this may limit their applicability in operating room environments. Additionally, they do not work for spontaneously breathing patients.

SUMMARY

Disclosed embodiments include a method for assessing fluid responsiveness implemented in a digital computer with one or more processors comprising: (a) measuring a cardiovascular signal, and (b) computing a dynamic index predictive of fluid responsiveness from said cardiovascular signal using a nonlinear state space estimator. According to one particular embodiment, and without limitation, the nonlinear state space estimator is based on a model for cardiovascular signals such as arterial blood pressure or plethysmogram signals, and uses a marginalized particle filter to estimate a dynamic index predictive of fluid responsiveness that is substantially equivalent to a variation in pulse pressure of said cardiovascular signal.

BRIEF DESCRIPTION OF THE DRAWINGS

Disclosed embodiments are illustrated by way of example, and not by way of limitation, in the figures of the accompanying drawings.

DETAILED DESCRIPTION

Figure 1:
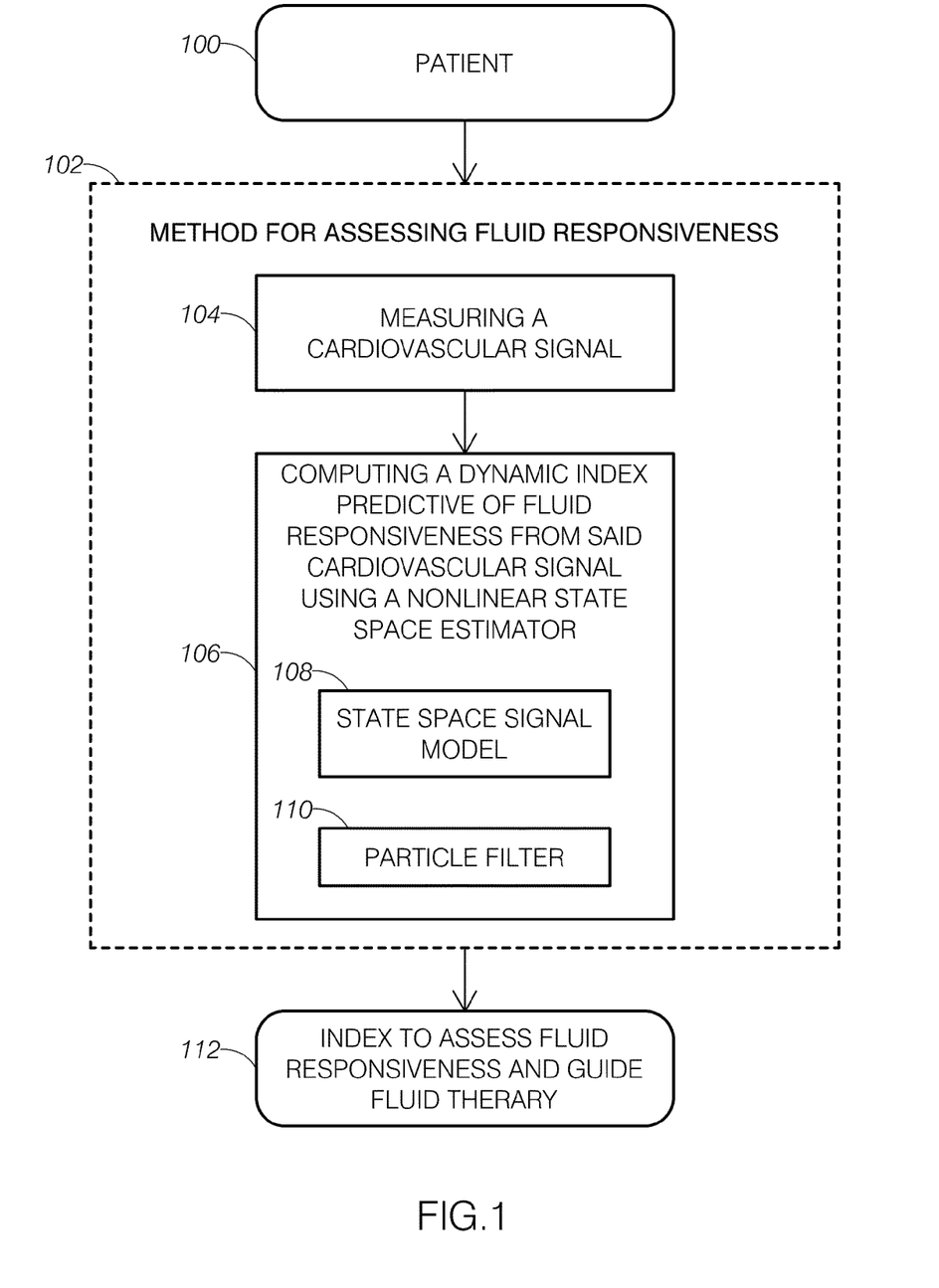
FIG. 1 shows a block diagram of the method according to one embodiment.

Disclosed embodiments include a method for assessing fluid responsiveness 102 implemented in a digital computer with one or more processors, said method comprising: (a) measuring a cardiovascular signal 104, and (b) computing a dynamic index predictive of fluid responsiveness from said cardiovascular signal using a nonlinear state space estimator 106. The cardiovascular signal can be arterial blood pressure (ABP), the photoplethysmographic signal (PLETH), central venous pressure (CVP), intracranial pressure (ICP), and others. According to one particular embodiment, and without limitation, the nonlinear state space estimator is based on a model for cardiovascular signals 108 such as arterial blood pressure or plethysmogram signals, and uses a marginalized particle filter 110 to estimate a dynamic index predictive of fluid responsiveness 112 that is substantially equivalent to a variation in pulse pressure of said cardiovascular signal. The method can be implemented as part of an medical monitoring apparatus for assessing fluid responsiveness, comprising: (a) a measuring unit (i.e. physiological signal acquisition sensors and analog to digital converters) for measuring a cardiovascular signal 104; and (b) a processing unit for computing a dynamic index predictive of fluid responsiveness from said cardiovascular signal using a nonlinear state space estimator 106. According to a specific embodiment, the method can be implemented in a medical system with one or more processors, physiological signal acquisition, analog to digital converters, memory, and output displays such as the typical bedside monitors used in clinical care. Alternatively, it can be implemented in a digital computer with one or more processors to analyze physiological signals and display or output, an indicator of fluid responsiveness that can be used to guide fluid therapy.

The following sections describe an embodiment of the a method for assessing fluid responsiveness 102 for the case of arterial blood pressure signals (ABP) and estimation of the pulse pressure variation index (PPV). Substantially equivalent embodiments without departing from the spirit of the disclosed embodiments are applicable to other cardiovascular signals and other derived parameters in addition to PPV. For instance, the state space model 108 and estimator 110 are applicable to the case of plethysmogram signals, and any other dynamic index predictive of fluid responsiveness substantially equivalent to a variation in pulse pressure of said cardiovascular signal due to respiration.

Certain specific details are set forth in the following description and figures to provide a thorough understanding of various embodiments disclosed. Certain well-known details often associated with computing and software technology are not set forth in the following disclosure to avoid unnecessarily obscuring the various disclosed embodiments. Further, those of ordinary skill in the relevant art will understand that they can practice other embodiments without one or more of the details described below. Aspects of the disclosed embodiments may be implemented in the general context of computer-executable instructions, such as program modules, being executed by a computer, computer server, or device containing a processor. Generally, program modules include routines, programs, objects, components, data structures, etc. that perform particular tasks or implement particular abstract data types. Aspects of the disclosed embodiments may also be practiced in distributed computing environments where tasks are performed by remote processing devices that are linked through a communications network. In a distributed computing environment, program modules may be located in both local and remote storage media including memory storage devices. Those skilled in the art will appreciate that, given the description of the modules comprising the disclosed embodiments provided in this specification, it is a routine matter to provide working systems which will work on a variety of known and commonly available technologies capable of incorporating the features described herein.

A. Mathematical Notation

In the detailed description of this application the following mathematical notation is used. The mathematical notation is thoroughly described in this section to aid those skilled in the art to understand, implement, and practice the disclosed embodiments. We use boldface to denote random processes, normal face for deterministic parameters and functions, upper case letters for matrices, lower case letters for vectors and scalars, superscripts in parenthesis for particle indices, uppercase superscripts for nonlinear/linear indication, and subscripts for time indices. For example, the nonlinear portion of the state vector for the $i^{th}$ state trajectory (i.e., particle) is denoted as $\chi_n^{N,(i)}$ where n represents the discrete time index and (i) denotes the $i^{th}$ particle. The unnormalized particle weights are denoted as $\tilde{w}^{(i)}$ and the normalized particle weights as $w^{(i)}$. The state trajectories before resampling are denoted as $\tilde{\chi}_n^{(i)}$ and as $\chi_n^{(i)}$ after resampling.

B. State-Space Model

According to one embodiment of the proposed method and apparatus for assessing fluid responsiveness 102, and without limitation, the method/apparatus utilizes a sequential Monte Carlo estimation method 110 which is based on the state-space model approach. The state-space model is a mathematical expression to describe the evolution of any physical system's unobservable state $\chi_n$ and its relation to measurement $y_n$, where the state $\chi_n$ is a vector of parameters representing the system's condition. The state-space method is a technique to estimate the state $\chi_n$ as a function of measurement $y_n$ utilizing the state-space model. The typical state-space model can be expressed as, $$\chi_{n+1} = f(\chi_n) + u_n \quad (2)$$

$$y_n = h(\chi_n) + v_n \quad (3)$$

where (2) is a process model, (3) a measurement model, $f(\bullet)$ and $h(\bullet)$ functions of the state $\chi_n$, and $u_n$ and $v_n$ uncorrelated white noise with variances q and r. A designer needs to incorporate prior domain knowledge of a system into the state-space model and define the functions $f(\cdot)$ and $h(\cdot)$. The flexibility and versatility of the state-space method are attributable to two functions, which can be either linear or nonlinear.

B.1. Measurement Model

According to one embodiment of the proposed method and apparatus for assessing fluid responsiveness 102, and without limitation, the measurement model of the cardiovascular signal is shown in (4)-(6), where $\gamma_n$ is the respiratory signal, $\mu_n$, the amplitude-modulated cardiac signal, $\rho_{k,n}$ the amplitude modulation factor of the $k^{th}$ cardiac harmonic partial, $\kappa_{k,n}$ the $k^{th}$ cardiac harmonic partial, $\theta_n^r$ the instantaneous respiratory angle, $\theta_n^c$ the instantaneous cardiac angle, $f_n^r$ the instantaneous respiratory rate, $N_h^r$ the number of respiratory partials, $N_h^c$ the number of cardiac partials, and $v_n$ the white Gaussian measurement noise with variance r.

$$y_n = \gamma_n + \mu_n + v_n = \gamma_n + \sum_{k=1}^{N_h^c} \rho_{k,n}\kappa_{k,n} + v_n \quad (4)$$

$$\gamma_n = \sum_{k=1}^{N_h^r} r_{1,k,n}\cos(k\theta_n^r) + r_{2,k,n}\sin(k\theta_n^r) \quad (5)$$

$$\rho_{k,n} = 1 + \sum_{j=1}^{N_h^r} m_{1,k,j,n}\cos(j\theta_n^r) + m_{2,k,j,n}\sin(j\theta_n^r) \quad (6)$$

$$\kappa_{k,n} = \sum_{k=1}^{N_h^c} c_{1,k,n}\cos(k\theta_n^c) + c_{2,k,n}\sin(k\theta_n^c) \quad (7)$$

B.2. Process Model

According to one embodiment of the proposed method and apparatus for assessing fluid responsiveness 102, and without limitation, the process model describes the evolution of each element of the state $\chi_n$. In our application, $\chi_n$ includes the instantaneous respiratory and cardiac angles $\theta_n^r$ and $\theta_n^c$, the instantaneous mean cardiac frequency $\bar{f}_n^c$, the instantaneous respiratory and cardiac frequencies $f_n^r$ and $f_n^c$, and the sinusoidal coefficients $\{r_{1,k,n}, r_{2,k,n}, c_{1,k,n}, c_{2,k,n}, m_{1,k,n}, m_{2,k,n}\}$. The process model can be expressed as, $$\theta_{n+1}^r = 2\pi(n+1)T_s f^r \quad (8)$$

$$\theta_{n+1}^c = \theta_n^c + 2\pi T_s f_n^c \quad (9)$$

$$\bar{f}_{n+1}^c = g[\bar{f}_n^c + u_{\bar{f},n}] \quad (10)$$

$$f_{n+1}^c = \bar{f}_n^c + \alpha(f_n^c - \bar{f}_n^c) + u_{f^c,n} \quad (11)$$

$$r_{\cdot,k,n+1} = r_{\cdot,k,n} + u_{r,n} \quad (12)$$

$$c_{\cdot,k,n+1} = c_{\cdot,k,n} + u_{c,n} \quad (13)$$

$$m_{\cdot,k,n+1} = m_{\cdot,k,n} + u_{m,n} \quad (14)$$

where $f^r$ is the constant respiratory frequency, $f_n^c$ the instantaneous cardiac frequency, $T_s$ the sampling period, $\bar{f}_n^c$ the instantaneous mean cardiac frequency, $\alpha$ the autoregressive coefficient, and $u_{r,n}$, $u_{c,n}$, and $u_{m,n}$ the process noises with variances $q_r$, $q_c$, and $q_m$. Since this process model is for ABP signals of patients with full mechanical support, the respiratory frequency $f^r$ has a known constant value. The clipping function $g[\cdot]$ limits the range of instantaneous mean frequencies, which can be written as, $$g[f] = \begin{cases} f_{max} - (f - f_{max}) & f_{max} < f \\ f & f_{min} < f \leq f_{max} \\ f_{min} + (f_{min} - f) & f \leq f_{min} \end{cases} \quad (15)$$

The range of instantaneous mean frequencies is assumed to be known as domain knowledge. Other functions could be used here that are generally sigmoidal in shape and limit the range of instantaneous frequencies such as arctangent and hyperbolic tangent functions.

C. State Estimation

According to one embodiment of the proposed method and apparatus for assessing fluid responsiveness 102, and without limitation, the nonlinear state space estimator is a sequential Monte Carlo method (SMCM). The SMCM is a computational Bayesian approach to estimation of an unknown state $\chi_n$, recursively given measurement $y_n$ and the state-space model. The SMCM estimates the posterior mean of the state $E[p(\chi_{0:n}|y_{0:n})]$ as a weighted sum of random samples $\chi_{0:n}^{(i)}$, which can be expressed as, $$E[p(x_{0:n}|y_{0:n})] = \sum_{i=1}^{N_p} x_{0:n}^{(i)} w_{0:n}^{(i)} \quad (16)$$

where $\chi_{0:n} = \{\chi_0, \ldots, \chi_n,\}$ and $w_{0:n}^{(i)}$ is the random sample weight. The SMCM is better known as a particle filter (PF), since the random samples are often referred to as particles. The proposed SMCM overcomes the limitations of the conventional SMCM such as sampling degeneracy and impoverishment issues. It also addresses properly the multi-modality issue of the posterior distribution $p(f_n|y_{0:n})$ where $f_n$ is the fundamental frequency of a multiharmonic signa. The proposed SMCM is called, maximum a-posteriori adaptive marginalized particle filter (MAM-PF). The method is described in detail in Table (Algorithm 1).

The MAM-PF ABP tracker continuously estimates the parameters of the process model shown in (8)-(13). The number of parameters to track is $4N_h^r + 2N_c^c + 1$. Obtaining accurate estimation of those parameters is the first step toward PPV index estimation.

D. ABP and Pleth Signal Envelope Estimation

Figure 2:
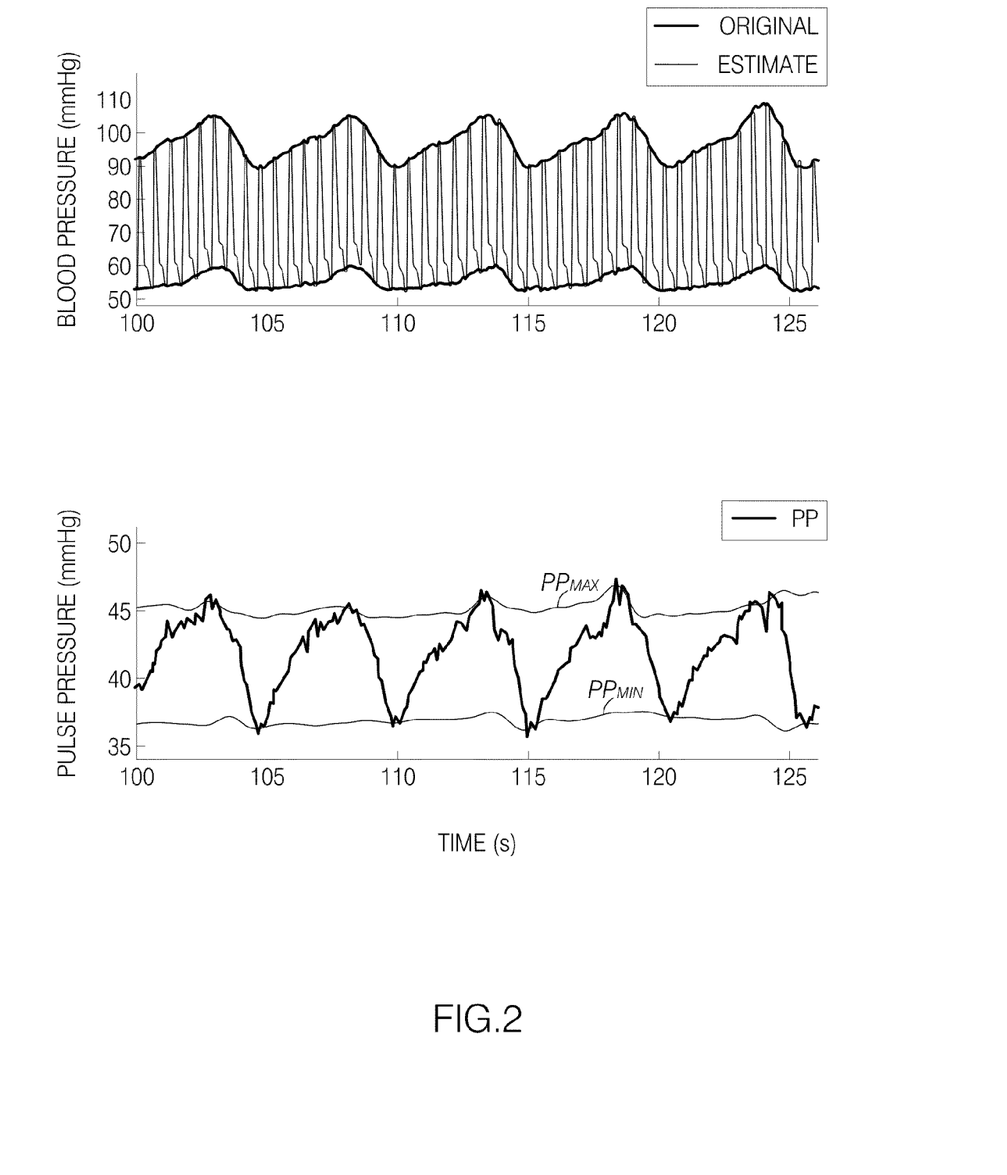
FIG. 2 shows an estimation example based on the state space model and estimator according to one embodiment.

Given the estimated signal parameters in (8)-(14), it is possible to estimate the upper envelope ($e_{\mu,n}$) and lower envelope ($e_{l,n}$) of ABP or pleth signals by following steps below, $$\theta_{max}^c = \arg\max_\theta \sum_{k=1}^{N_h^c} \rho_{k,n}[c_{1,k,n}\cos(k\theta) + c_{2,k,n}\sin(k\theta)]$$

$$\theta_{min,n}^c = \arg\min_\theta \sum_{k=1}^{N_h^c} \rho_{k,n}[c_{1,k,n}\cos(k\theta) + c_{2,k,n}\sin(k\theta)]$$

$$\kappa_{max,k,n} = c_{1,k,n}\cos(k\theta_{max,n}^c) + c_{2,k,n}\sin(k\theta_{max,n}^c)$$

$$\kappa_{min,k,n} = c_{1,k,n}\cos(k\theta_{min,n}^c) + c_{2,k,n}\sin(k\theta_{min,n}^c)$$

$$e_{\mu,n} = \gamma_n + \sum_{k=1}^{N_h^c} \rho_{k,n}\kappa_{max,k,n} \quad (17)$$

$$e_{l,n} = \gamma_n + \sum_{k=1}^{N_h^c} \rho_{k,n}\kappa_{min,k,n} \quad (18)$$

where $\arg\max_\chi f(\chi)$ and $\arg\min_\chi f(\chi)$ are operators to obtain the value of $\chi$ for which $f(\chi)$ attains its maximum and minimum values, respectively. The top plot in FIG. 2 shows a five respiratory cycle period of an ABP signal $y_n$, its estimate $\hat{y}_n$, and its estimated envelopes $e_{\mu,n}$ and $e_{l,n}$.

| Algorithm 1 Table-MAM-PF Method Steps |
|---|
| Initialization |
|   for i = 1, ... , $N_p$ do |
|     Sample $x_0^{N,(i)} \sim \pi_0(x_0^N)$ |
|     $\hat{x}_{0:-1}^{L,(i)} = E[x_0^{L,(i)} \mid x_0^{N,(i)}]$ |
|   end for |
|   for i = 1, ... , $N_p$ do |
|     $\alpha_0^{(i)} = \pi_0(x_0^{N,(i)})p(y_0 \mid x_0^{N,(i)}, x_0^{L,(i)})$ |
|     $z_0^{(i)} = x_0^{(i)}$ |
|   end for |
|   $i^* = \arg\max_i \alpha_0^{(i)}$ & $\hat{x}_0 = x_0^{i^*}$ |
| for n = 1, ... , $N_T$ do |
|   for i = 1, ... , $N_p$ do |
|     MAP Estimation |
|     Particle Propagation |
|     $x_n^{N,(i)} \sim q_n(x_n^{N,(i)} \mid x_{n-1}^{N,(i)}, y_n)$ |
|     $k^* = \arg\max_k \alpha_{n-1}^{(k)} p(x_n^{N,(i)} \mid x_{n-1}^{N,(k)})$ |
|     Marginalized Sequential Estimation |
|     Measurement Update |
|     $\hat{y}_{n\mid 0:n-1} = H_n(x_n^{N,(i)})\hat{x}_{n\mid 0:n-1}^{L,(k^*)}$ |
|     $e_n = y_n - \hat{y}_{n\mid 0:n-1}$ |
|     $R_{v,n} = [e_n e_n^T - H_n(x_n^{N,(i)})C_{n\mid 0:n-1}^{(k^*)} H_n(x_n^{N,(i)})^T]_+$ |
|     $\hat{R}_{v,n} = \beta \hat{R}_{v,n-1}^{(k^*)} + (1-\beta)R_{v,n}$ |
|     $R_{e,n} = H_n(x_n^{N,(i)})C_{n\mid 0:n-1}^{(k^*)} H_n(x_n^{N,(i)})^T + \hat{R}_{v,n}$ |
|     $K_n = C_{n\mid 0:n-1}^{(k^*)} H_n(x_n^{N,(i)})^T (R_{e,n})^{-1}$ |
|     $\hat{x}_{n\mid 0:n}^L = \hat{x}_{n\mid 0:n-1}^{L,(k^*)} + K_n e_n$ |
|     $C_{n\mid 0:n} = [I - K_n H_n(x_n^{N,(i)})]C_{n\mid 0:n-1}^{(k^*)}$ |
|     Time Update |
|     $\hat{R}_{v,n}^{(i)} = \hat{R}_{v,n}$ |
|     $\hat{x}_{n+1\mid 0:n}^{L,(i)} = F_n(x_n^{N,(i)})\hat{x}_{n\mid 0:n}^L$ |
|     $C_{n+1\mid 0:n}^{(i)} = F_n(x_n^{N,(i)})C_{n\mid 0:n}F_n(x_n^{N,(i)})^T + Q_u^L$ |
|     $\alpha_n^{(i)} = \alpha_{n-1}^{(k^*)} p(y_n \mid x_n^{N,(i)}, \hat{x}_{n\mid 0:n-1}^{L,(k^*)}) p(x_n^{N,(i)} \mid x_{n-1}^{N,(k^*)})$ |
|     $\hat{x}_n^{(i)} = [\hat{x}_{n\mid 0:n}^L, x_n^{N,(i)}]^T$ |
|     $z_{0:n}^{(i)} = [z_{0:n-1}^{(k^*)}, \hat{x}_n^{(i)}]$ |
|   end for |
|   Update MAP State Estimate |
|   $i^* = \arg\max_i \alpha_n^{(i)}$ |
|   $\hat{x}_{0:n} = z_{0:n}^{i^*}$ |
| end for |

E. Pulse Pressure Signal Envelope Estimation

The pulse pressure (PP) signal is the difference between the upper envelope $e_{\mu,n}$ and lower envelope $e_{l,n}$ of the cardiovascular pressure signal (ABP, ICP, pleth, ECG, etc). This PP signal oscillates roughly at the respiratory rate as shown in the bottom plot in FIG. 2. This oscillation is due to the respiratory effect on the variation of systemic ABP under full ventilation support. Within each respiratory cycle PP reaches its maximum ($PP_{max}$) and minimum ($PP_{min}$) values, which are two critical parameters to compute the PPV index.

Traditionally, the $PP_{max}$ and $PP_{min}$ values have been computed only once per each respiratory cycle. Given the estimated signal parameters in (8)-(14), however, according to one embodiment, the continuous equivalents of $PP_{max}$ and $PP_{min}$ are computed. They are the upper $\epsilon_{\mu,n}$ and lower $\epsilon_{l,n}$ envelopes of the PP signal. The upper envelope is the continuous estimate of $PP_{max}$ and the lower envelope $\epsilon_{l,n}$ that of $PP_{min}$. The $\epsilon_{\mu,n}$ and $\epsilon_{l,n}$ values can be estimated as described below, $$\varrho_{k,n} = \sum_{j=1}^{N_h^r} m_{1,k,j,n} \cos(j\theta) + m_{2,k,j,n} \sin(j\theta)$$

$$\theta_{max,n}^r = \arg\max_\theta \sum_{k=1}^{N_h^c} (1 + \varrho_{k,n})(\kappa_{max,k,n} - \kappa_{min,k,n})$$

$$\theta_{min,n}^r = \arg\min_\theta \sum_{k=1}^{N_h^c} (1 + \varrho_{k,n})(\kappa_{max,k,n} - \kappa_{min,k,n})$$

$$\varrho_{max,k,n} = \sum_{j=1}^{N_h^r} m_{1,k,j,n} \cos(j\theta_{max,n}^r) + m_{2,k,j,n} \sin(j\theta_{max,n}^r)$$

$$\varrho_{min,k,n} = \sum_{j=1}^{N_h^r} m_{1,k,j,n} \cos(j\theta_{min,n}^r) + m_{2,k,j,n} \sin(j\theta_{min,n}^r)$$

$$\varepsilon_{\mu,n} = \sum_{k=1}^{N_h^c} (1 + \varrho_{max,k,n})(\kappa_{max,k,n} - \kappa_{min,k,n}) \quad (19)$$

$$\varepsilon_{l,n} = \sum_{k=1}^{N_h^c} (1 + \varrho_{min,k,n})(\kappa_{max,k,n} - \kappa_{min,k,n}) \quad (20)$$

where $1 + \varrho_{k,n}$ is equal to $\rho_{k,n}$, and $\epsilon_{\mu,n}$ and $\epsilon_{l,n}$ are the continuous estimates of the $PP_{max}$ and $PP_{min}$, respectively. The lines in the bottom plot in FIG. 2 represent the upper $\epsilon_{\mu,n}$ and lower $\epsilon_{l,n}$ envelopes of the PP signal obtained by following the method described above.

F. Pulse Pressure Variation Calculation

According to one embodiment of the proposed method and apparatus for assessing fluid responsiveness 102, and without limitation, given the $\epsilon_{\mu,n}$ and lower $\epsilon_{l,n}$ values, the PPV index is calculated directly as follows, $$PPV(\%) = 100 \times \frac{\varepsilon_{max} - \varepsilon_{min}}{(\varepsilon_{max} + \varepsilon_{min}/2)} \quad (21)$$

According to one embodiment, PPV is typically calculated over several respiratory cycles (at least one cycle is required). This new PPV index is different from the traditional PPV index described in (1) because the new one is continuous in time while the traditional one can be obtained only once per each respiratory cycle.

Figure 3:
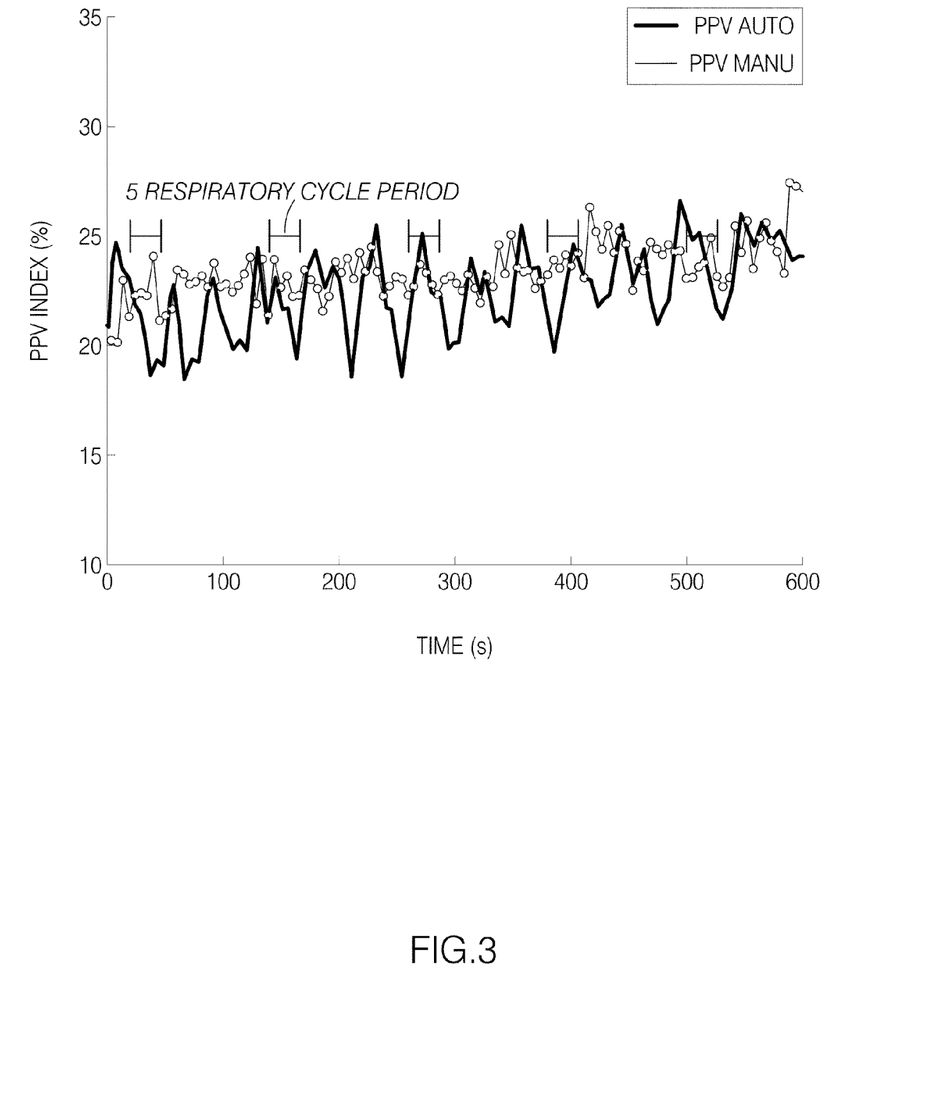
FIG. 3 shows an estimation example of PPV based on the state space model and estimator according to one embodiment.

FIG. 3 illustrates an example of the automatically computed continuous PPV index and the manually obtained discrete PPV index of a real 10 min ABP signal. Each hollow white dot represents a "discrete" PPV index, which can be obtained once per each respiratory cycle.

G. Validation and Testing of the Method According to One Embodiment.

The following description presents the experimental results and tests of a prototype according to a disclosed embodiment.

G.1. Method Validation: Assessment Data The Massachusetts General Hospital (MGH) waveform database on PhysioNet is a comprehensive collection of electronic recordings of hemodynamic and electrocardiographic waveforms patients in critical care units. It consists of recordings from 250 patients representing

TABLE 1

Summary of user-specified design parameters for the PPV index estimator

Figure 4:
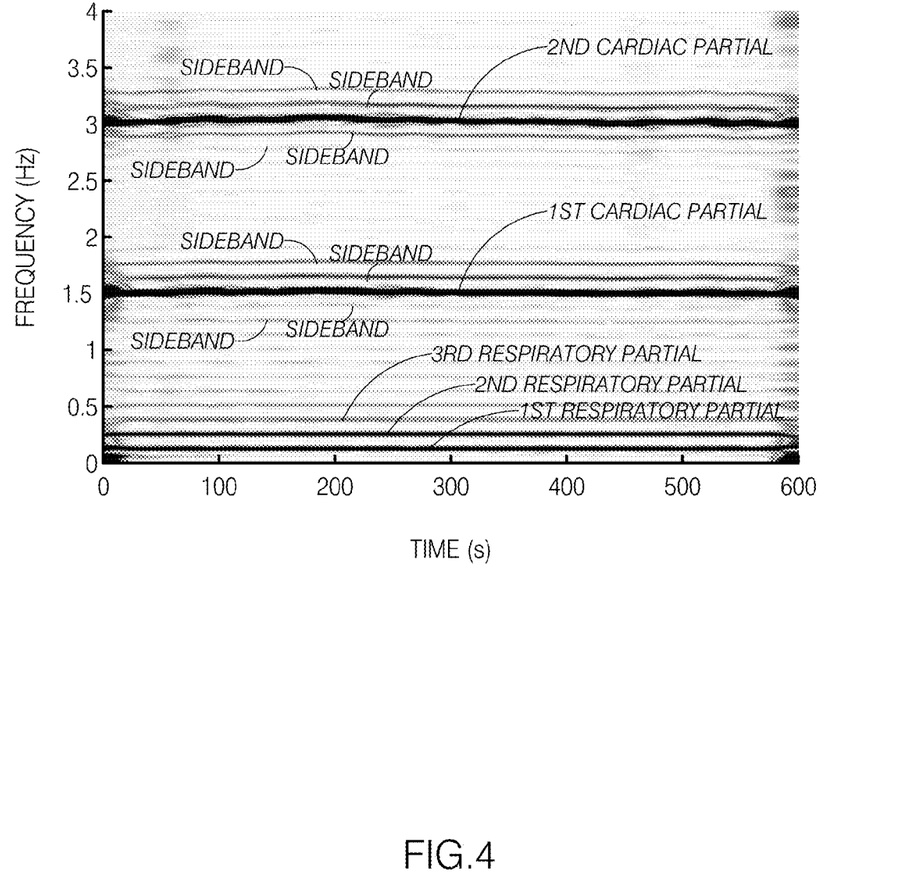
FIG. 4 shows a spectrogram of a sample signal used in the assessment dataset.

| Name | Symbol | Value |
| --- | --- | --- |
| No. particles | $N^p$ | 250 |
| No. cardiac components | $N^c$ | 10 |
| No. respiratory components | $N^r$ | 3 |
| Minimum heart rate | $f_{min}^c$ | 50/60 Hz |
| Maximum heart rate | $f_{max}^c$ | 150/60 Hz |
| Measurement noise variance | r | var(y)/1e3 |
| Cardiac frequency variance | $q_f^c$ | 7e–6 $T_s$ |
| Respiratory amplitude variance | $q_a \& q_b$ | 1e–5 $T_s$ |
| Modulation factor amplitude variance | $q_c \& q_d$ | 1e–9 $T_s$ |
| Cardiac amplitude variance | $q_e \& q_f$ | 1e–6 $T_s$ |
| Initial respiratory amplitude | $u_a \& u_b$ | std(y)/1e2 |
| Initial modulation factor amplitude | $u_c \& u_d$ | std(y)/1e2 |
| Initial cardiac amplitude | $u_e \& u_f$ | std(y) | a broad spectrum of physiologic and pathophysiologic states. The typical recording includes arterial blood pressure (ABP) signals in addition to seven other types of waveforms. By visually inspecting the spectrogram of ABP signals we identified 26 patients whose respiratory rate remained constant at least for 10 consecutive minutes. We used the constant respiratory rate shown in spectrogram as an indicator of full respiratory support. FIG. 4 shows the spectrogram of one of the 26 ABP signals. The total duration of the 26 ABP signals was a little bit over 4 hours (260 min). The original sample rate $f_s$ of the signals was 360 Hz, but they were downsampled by a factor of 9, so that the final sample rate $f_s$ was 40 Hz.

Typically the constant respiratory rate $f^r$ of subjects under full ventilation support is easily accessible medical information since it is equal to the machine ventilation rate.

In this embodiment, the number of cardiac components $N^c$ was 10 and that of respiratory components $N^r$ 3. The number of particles was 250. Table 1 lists the parameter values used for the PPV index estimator.

G.2. Method Validation: Manual PPV Annotations (Gold Standard)

We manually detected the peaks and troughs of the ABP signals and calculated the PPV indices (gold standard) as defined in (1). They are referred to as manual PPV indices $PPV_{manu}$. $PPV_{auto}$ represents PPV indices obtained using the proposed PPV index tracking algorithm.

We had to exclude 3 ABP signals out of the 26 ABP signals from our validation study because it was not possible to annotate either those 3 ABP signals or their PP signals due to a high noise level or abnormal cardiac activity.

G.3. Method Validation: Statistical Analysis

We took 5 PPV index measurements per subject separately by 2 min. Each PPV index measurement is an averaged value over 5 respiratory cycles. FIG. 3 shows the 2 min apart measurement periods. The proposed PPV index tracking algorithm was assessed by calculating the agreement (mean±standard deviation) between $PPV_{auto}$ and $PPV_{manu}$ measurements and using Bland-Altman analysis.

A Bland-Altman plot is a statistical and visualization method that is often used in the assessment of PPV estimation method in order to determine the agreement between two different PPV estimates across the PPV range. It shows the difference $\Delta PPV$ between $PPV_{auto}$ and $PPV_{manu}$ on the y-axis and the $PPV_{manu}$ on the x-axis. It visualizes not only the overall accuracy of estimation but also any estimation bias or trend versus $PPV_{manu}$. We used it to compare the gold standard using manual annotations with our automatic estimation algorithm.

G.4. Method Validation: Results

Figure 5:
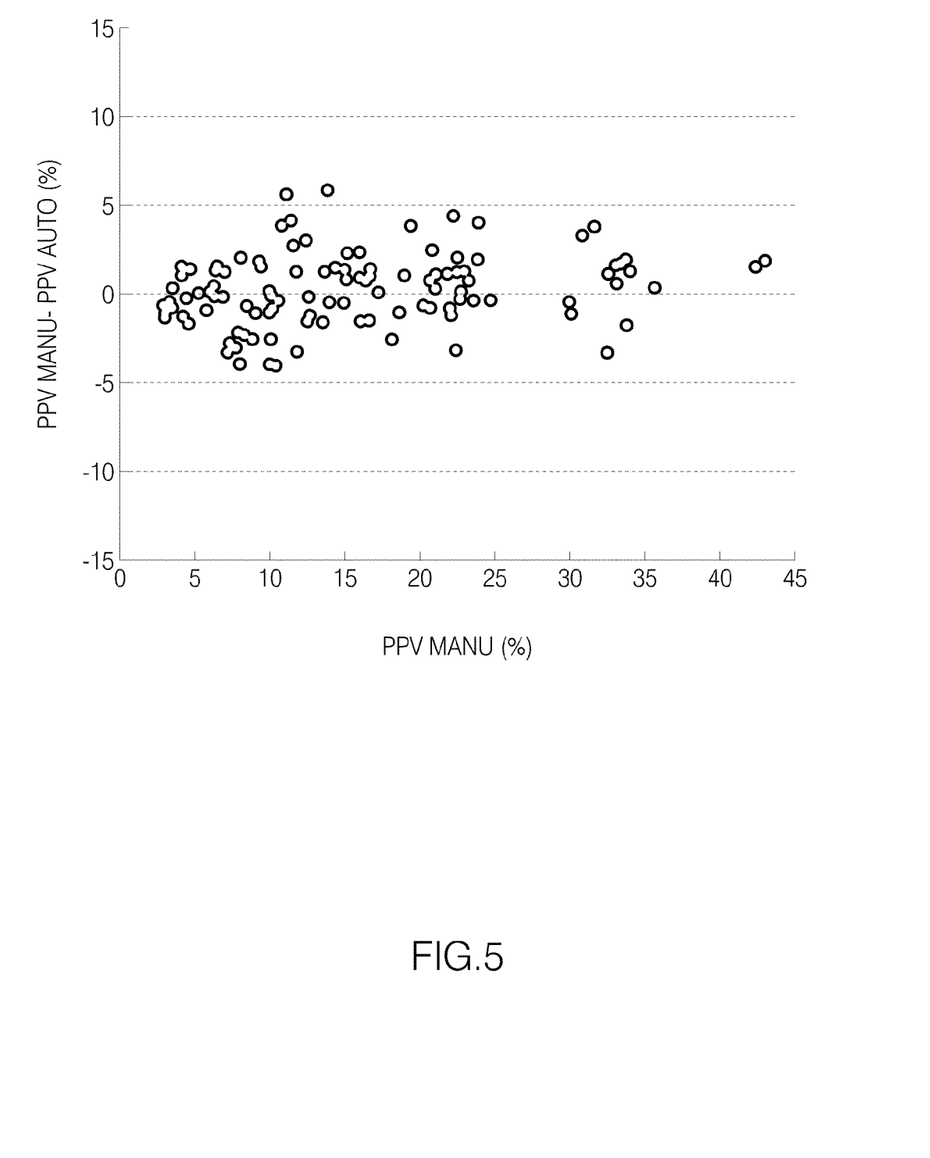
FIG. 5 shows the performance results of the proposed method for PPV estimation according to one embodiment.

FIG. 5 depicts the Bland-Altman plot of the 23 subjects. There are 5 PPV measurements available per each subject. In this embodiment, most (98%) of $PPV_{auto}$ measurements were in agreement with $PPV_{manu}$ measurements within ±5% accuracy, and 100% within ±8% accuracy.

TABLE 2

Summary of the mean and standard deviation of the $PPV_{manu}$ and $PPV_{auto}$

| Subject | $PPV_{manu}$ (%) | $PPV_{auto}$ (%) |
| --- | --- | --- |
| 1 | 23.2 ± 1.0 | 23.6 ± 1.0 |
| 2 | 23.0 ± 0.3 | 22.8 ± 1.6 |
| 3 | 13.7 ± 0.8 | 14.3 ± 1.2 |
| 4 | 12.3 ± 1.1 | 9.1 ± 3.1 |
| 5 | 36.3 ± 5.9 | 33.9 ± 6.7 |
| 6 | 8.7 ± 1.8 | 9.5 ± 2.0 |
| 7 | 18.2 ± 2.6 | 18.8 ± 1.7 |
| 8 | 6.3 ± 1.3 | 6.2 ± 0.8 |
| 9 | 9.6 ± 1.7 | 7.1 ± 0.8 |
| 10 | 15.9 ± 0.8 | 14.8 ± 0.8 |
| 11 | 5.3 ± 1.0 | 5.5 ± 0.7 |
| 12 | 3.1 ± 0.2 | 4.0 ± 0.3 |
| 13 | 31.8 ± 1.6 | 31.5 ± 0.8 |
| 14 | 15.3 ± 2.8 | 13.1 ± 1.8 |
| 15 | 33.9 ± 1.1 | 34.3 ± 1.8 |
| 16 | 4.6 ± 1.1 | 3.4 ± 1.0 |
| 17 | 20.4 ± 2.3 | 20.1 ± 2.7 |
| 18 | 9.8 ± 0.8 | 11.9 ± 2.2 |
| 19 | 9.6 ± 2.1 | 11.2 ± 1.4 |
| 20 | 11.9 ± 0.5 | 10.3 ± 1.2 |
| 21 | 8.7 ± 1.8 | 11.9 ± 1.9 |
| 22 | 21.7 ± 1.9 | 18.9 ± 1.2 |
| 23 | 20.9 ± 2.1 | 20.0 ± 0.7 |

Table 2 lists the mean±standard deviation of 5 $PPV_{manu}$ and $PPV_{auto}$ measurements for each subject. The second column is for $PPV_{manu}$ and the third column for $PPV_{auto}$.

A design difference of the proposed method with respect to previously published method is the fact that the proposed method is based on a statistical state-space model and estimation of the cardiovascular pressure pressure signal. The state-space modeling stage results in an algorithm that is more robust to hemodynamic changes and artifacts. The statistical state-space signal model and associated model parameter estimation algorithm automatically filter out noise and artifact that cannot be captured with the model. Since the statistical signal model is based on cardiovascular physiology and pathophysiology, signal features that are not physiological in nature are automatically filtered out. Additionally, the model is general enough to accurately model both arterial blood pressure signals and plethysmogram signals. Consequently, it can also be used to calculate the pleth variability index (PVI).

Figure 6:
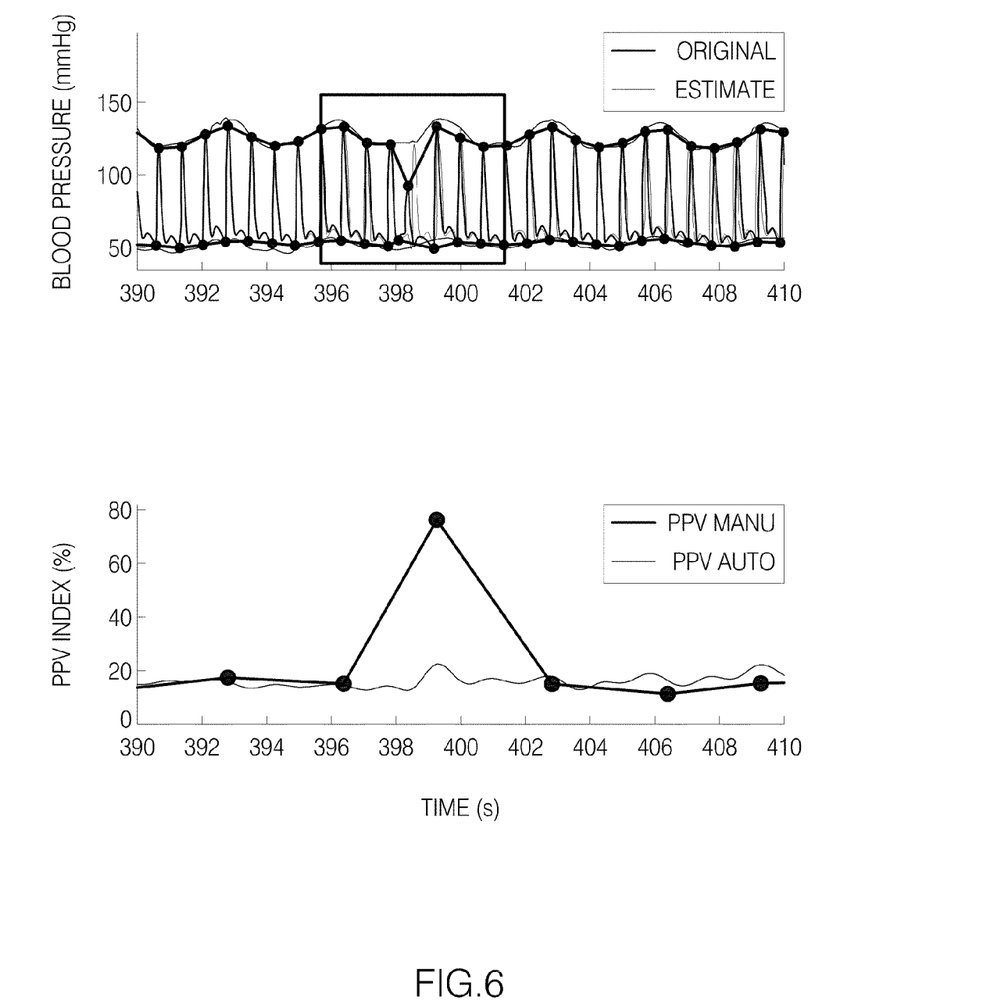
FIG. 6 illustrates the process of automatic PPV estimation during artifacts according to one embodiment.
Figure 7:
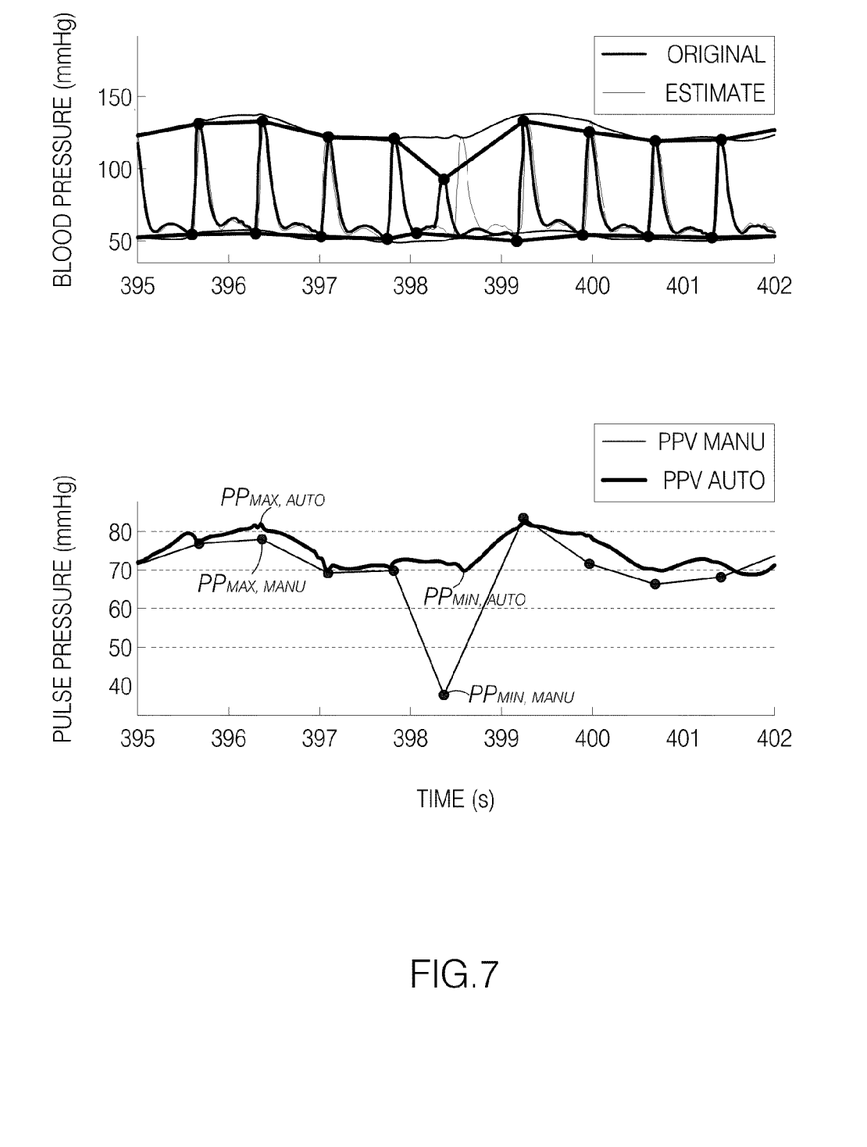
FIG. 7 illustrates the process of automatic PPV estimation during artifacts according to one embodiment.

FIG. 6 and FIG. 7 exemplify a case where signal features that are not physiological in nature are automatically filtered out resulting in more accurate PPV index estimation than manual annotation. The top plot in FIG. 6 illustrates 6 respiratory cycles of the ABP signal of Subject 3 and its estimate. It also shows the manually annotated signal envelopes and the automated computed signal envelopes. The bottom plot in FIG. 7 depicts the $PPV_{manu}$ and $PPV_{auto}$ over the same period. Around 399 s, the $PPV_{manu}$ value abruptly increases up to 78% while the $PPV_{auto}$ value remains at 20%. Around 403 s, the $PPV_{manu}$ value returns to 20%. FIG. 7 focuses on the time period marked with the black rectangular box in FIG. 6. The top plot in FIG. 7 shows that the heart beat between 398 s and 399 s is irregular and abnormal. As a result, the corresponding $PP_{manu}$ shown in the bottom plot reaches a very small minimum value ($PP_{min,manu}$: 38%) between 398 s and 399 s. However, the automatically computed minimum PP value ($PP_{min,auto}$) over the same period is as high as 70%. This discrepancy between the manual annotation and the proposed automatic method results from the capability of the MAM-PF algorithm, which estimates the ABP signal based on the state-space model. While the original heart beat 398 s and 399 s in FIG. 6 is abnormal in a physiological sense, the estimated heart beat over the same time period shows the physiologically expected morphology and location of the heart beat.

H. Method for Assessing Fluid Responsiveness in Spontaneously Breathing Patients According to one embodiment, the method and apparatus for assessing fluid responsiveness is adapted to work for spontaneously breathing patients (i.e. patients not mechanically ventilated). In this section we describe an embodiment for spontaneously breathing patients. Fluid responsiveness prediction in spontaneously breathing subjects is difficult. Since the swings in intrathoracic pressure are minor during spontaneous breathing, dynamic parameters like pulse PPV and systolic pressure variation (SPV) are usually small and more difficult to calculate.

H.1. Measurement Model

According to one embodiment, the measurement model of the ABP signal is shown in (22)(25), where $\gamma_n$ is the respiratory signal, $\mu_n$ the amplitude-modulated cardiac signal, $\rho_{k,n}$ the amplitude modulation factor of the $k^{th}$ cardiac harmonic partial, $\kappa_{k,n}$ the $k^{th}$ cardiac harmonic partial, $\theta_n^r$ the instantaneous respiratory angle, $\theta_n^c$ the instantaneous cardiac angle, $f_n^r$ the instantaneous respiratory rate, $N_h^r$ the number of respiratory partials, $N_h^c$ the number of cardiac partials, and $v_n$ the white Gaussian measurement noise with variance r.

$$y_n = \gamma_n + \mu_n + v_n = \gamma_n + \sum_{k=1}^{N_h^c} \rho_{k,n}\kappa_{k,n} + v_n \quad (22)$$

$$\gamma_n = \sum_{k=1}^{N_h^r} r_{1,k,n}\cos(k\theta_n^r) + r_{2,k,n}\sin(k\theta_n^r) \quad (23)$$

$$\rho_{k,n} = 1 + \sum_{j=1}^{N_h^r} m_{1,k,j,n}\cos(j\theta_n^r) + m_{2,k,j,n}\sin(j\theta_n^r) \quad (24)$$

$$\kappa_{k,n} = \sum_{k=1}^{N_h^c} c_{1,k,n}\cos(k\theta_n^c) + c_{2,k,n}\sin(k\theta_n^c) \quad (25)$$

H.2. Process Model

The process model describes the evolution of each element of the state $\chi_n$. In our application, $\chi_n$ includes the instantaneous respiratory and cardiac angles $\theta_n^r$ and $\theta_n^c$, the instantaneous mean respiratory $\bar{f}_n^r$ and cardiac $\bar{f}_n^c$ frequency, the instantaneous respiratory $f_n^r$ and cardiac $f_n^c$ frequencies, and the sinusoidal coefficients $\{r_{1,k,n}, r_{2,k,n}, c_{1,k,n}, c_{2,k,n}, m_{1,k,n}, m_{2,k,n}\}$. The process model can be expressed as, $$\theta_{n+1}^r = \theta_n^r + 2\pi T_s f_n^r \quad (26)$$

$$\theta_{n+1}^c = \theta_n^c + 2\pi T_s f_n^c \quad (27)$$

$$\bar{f}_{n+1}^r = g[\bar{f}_n^r + u_{\bar{f}^r,n}] \quad (28)$$

$$\bar{f}_{n+1}^c = g[\bar{f}_n^c + u_{\bar{f}^c,n}] \quad (29)$$

$$f_{n+1}^r = \bar{f}_n^r + \alpha(f_n^r - \bar{f}_n^r) + u_{f^r,n} \quad (30)$$

$$f_{n+1}^c = \bar{f}_n^c + \alpha(f_n^c - \bar{f}_n^c) + u_{f^c,n} \quad (31)$$

$$r_{\cdot,k,n+1} = r_{\cdot,k,n} + u_{r,n} \quad (32)$$

$$c_{\cdot,k,n+1} = c_{\cdot,k,n} + u_{c,n} \quad (33)$$

$$m_{\cdot,k,n+1} = m_{\cdot,k,n} + u_{m,n} \quad (34)$$

where $f_n^r$ is the instantaneous respiratory frequency, $f_n^c$ the instantaneous cardiac frequency, $T_s$ the sampling period, $\bar{f}_n^r$ the instantaneous mean respiratory frequency, $\bar{f}_n^c$ the instantaneous mean cardiac frequency, $\alpha$ the autoregressive coefficient, and $u_{r,n}, u_{c,n}$, and $u_{m,n}$ the process noises with variances $q_r, q_c$, and $q_m$. The clipping function $g[\cdot]$ limits the range of instantaneous mean frequencies, which can be written as, $$g[f] = \begin{cases} f_{max} - (f - f_{max}) & f_{max} < f \\ f & f_{min} < f \le f_{max} \\ f_{min} + (f_{min} - f) & f \le f_{min}. \end{cases} \quad (35)$$

The range of instantaneous mean frequencies is assumed to be known as domain knowledge.

H.3. Maximum A-Posteriori MPF

The proposed automated PPV index estimation method requires accurate estimates of the instantaneous respiratory frequency $f_n^r$, the instantaneous cardiac frequency $f_n^c$, and the morphology of an ABP signal. Within the state-space method framework, the Optimal MAM-PF computes the "optimal" trajectory of the state $\chi_n$. The Fast MAM-PF is an approximation of the Optimal MAM-PF, which requires dramatically less computational burden. However, the Fast MAM-PF performs as well as the Optimal MAM-PF. Under full mechanical support, the respiratory rate of subjects is equal to the mechanical ventilation rate, which is known and constant. Therefore, the Fast MAM-PF has to track only the instantaneous cardiac frequency $f_n^c$ along with the signal morphology.

The ABP signal tracker has to track both the instantaneous respiratory frequency $f_n^r$ and the instantaneous cardiac frequency $f_n^c$ along with the signal morphology. Although the Fast MAM-PF based ABP signal tracker is capable of tracking multiple frequencies, there are two major issues in using the Fast MAM-PF algorithm as the ABP signal tracker for ABP signals of spontaneously breathing subjects. The first issue is that the morphology of the signal, which is represented by the sinusoidal coefficients in (24)-(25), does not belong to the linear state any more. Since the modulating signal $\rho_{k,n}$ is multiplied to the cardiac signal $\kappa_{k,n}$, their sinusoidal coefficients $c_{\cdot,k,n}$ and $m_{\cdot,k,j,n}$ are nonlinear parameters of the measurement model in (22). The Fast MAM-PF is applicable only to state-space models whose state vector can be partitioned into the linear and nonlinear portions. The second issue is that the computational burden of the Fast MAM-PF increases exponentially as the dimension of the state where particle filters are used increases. The portion of the state space where particle filters are used is called the particle space. Since the new ABP signal tracker has to estimate both the instantaneous respiratory frequency $f_n^r$ and the instantaneous cardiac frequency $f_n^c$, the dimension of the particle state becomes 2, which results in a quadruple increase of computational burden if the Fast MAM-PF has to be used for the current application. Nevertheless, it is a possible embodiment that may be useful in certain situations. In order to address these two major issues we propose a new ABP signal tracker, which is a modified version of the Fast MAM-PF. It is called, the Dual MAM-PF. The term "Dual" reflects the fact that the particle space is two-dimensional. While the Fast MAM-PF treats a two-dimensional particle space as a whole, the Dual MAM-PF partitions the two-dimensional particle space into two one-dimensional particle spaces assuming independence between two particle space variables, which are the instantaneous respiratory frequency $f_n^r$ and the instantaneous cardiac frequency $f_n^c$.

Suppose that the state vector $\chi$ can be partitioned as follows, $$x_n = \begin{bmatrix} x_n^P \\ x_n^K \end{bmatrix} \tag{36}$$

where $\chi_n^P$ represents the particle state and $\chi_n^K$ the Kalman state. The particle state is the portion of the state where particle filters are used as defined earlier while the Kalman state is the portion of the state where extended Kalman filters are used. The state variables whose posterior distributions are known to be multi-modal belong to the particle state while those whose posterior distributions are known to be Gaussian or uni-modal belong to the Kalman state. Given the state-space model in (4)-(7), instantaneous respiratory frequency $f_n^r$ and the instantaneous cardiac frequency $f_n^c$ are the particle state variables and the sinusoidal coefficients such as $r_{\cdot,k,n}$, $c_{\cdot,k,n}$, and $m_{\cdot,k,j,n}$ are the Kalman state variables. Assuming that the particle state variables are independent of each other the particle state $\chi_n^P$ can be partitioned further as, $$x_n^P = \begin{bmatrix} x_n^{P_1} \\ x_n^{P_2} \end{bmatrix} \tag{37}$$

$$x_{n+1}^{P_1} = f_{1,n}(x_n^{P_1}, u_n^{P_1}) \tag{38}$$

$$x_{n+1}^{P_2} = f_{2,n}(x_n^{P_2}, u_n^{P_2}) \tag{39}$$

where $\chi_n^{P_1}$ and $\chi_n^{P_2}$ represent the first and second particle state variables, respectively. This partitioning breaks down a two-dimensional particle space $\chi_n^P$ into two one-dimensional particle spaces. The total posterior distribution is given by, $$p(x_{0:n} | y_{0:n}) = p(x_{0:n}^K | y_{0:n}, x_{0:n}^P) p(x_{0:n}^P | y_{0:n}) \tag{40}$$

$$= p(x_{0:n}^K | y_{0:n}, x_{0:n}^P) p(x_{0:n}^{P_1} | y_{0:n}) p(x_{0:n}^{P_2} | y_{0:n}). \tag{41}$$

Algorithm 2 provides a complete description of the Dual MAM-PF algorithm, where $N_T$ represents the total number of signal samples, $N_p$ the number of particles for each one-dimensional particle space, j the particle state variable index, and $i_j$ the particle index of the $j^{th}$ particle state variable. The total number of particle used in the Dual MAM-PF algorithm is $2N_p$ instead of $N_p^2$. At each time step n the Dual MAM-PF searches for the best trajectory of each particle $i_j$ from the previous trajectory. This searching step can be written as, $$k_j^* = \operatorname*{argmax}_{k_j} \alpha_{j,n-1}^{(k,j)} p\left(y_n \mid x_n^{P_j,(i_j)}, \hat{x}_{n|0:n-1}^{K,(k_j)}\right) \cdots \tag{42}$$

$$p\left(x_n^{P_j,(i_j)} \mid x_{n-1}^{P_j,(k_j)}\right)$$

$$\approx \operatorname*{argmax}_{k_j} \alpha_{j,n-1}^{(k,j)} p\left(y_n \mid x_n^{P_j,(i_j)}, \hat{x}_{n|0:n-1}^{K,(i_j)}\right) \cdots \tag{43}$$

$$p\left(x_n^{P_j,(i_j)} \mid x_{n-1}^{P_j,(k_j)}\right)$$

$$= \operatorname*{argmax}_{k_j} \alpha_{j,n-1}^{(k,j)} p\left(x_n^{P_j,(i_j)} \mid x_{n-1}^{P_j,(k_j)}\right). \tag{44}$$

Given the best trajectory for each particle $i_j$, corresponding Kalman state variables $\chi^{P_j,(i_j)}$, i.e. sinusoidal coefficients, are updated utilizing the extended Kalman filter. Then, the MAP estimate of $\chi_n^{P_j}$ is obtained based on the value of the coefficient $\alpha_{j,n}^{(i_j)}$ as follows, $$i_{j,n}^* = \operatorname*{argmax}_{i_j} \alpha_{j,n}^{(i_j)} \tag{45}$$

$$\hat{x}_n^{P_j} = x_n^{P_j,(i_{j,n}^*)} \tag{46}$$

Since there are two groups of particles $i_1$ and $i_2$, we need to select the best estimate of the Kalman state vector $\chi_n^K$ among two potential estimates: $\chi_n^{K,(i_{1,n}^*)}$ and $\chi_n^{K,(i_{2,n}^*)}$. The actual estimate of the Kalman state vector $\chi_n^K$ can be selected as follows, $$i_{MAP,n}^* = \begin{cases} i_{1,n}^* & \alpha_{1,n}^{(i_{1,n}^*)} \geq \alpha_{2,n}^{(i_{2,n}^*)} \\ i_{2,n}^* & \alpha_{1,n}^{(i_{1,n}^*)} < \alpha_{2,n}^{(i_{2,n}^*)} \end{cases}. \tag{47}$$

$$\hat{x}_n^K = x_n^{K,(i_{MAP,n}^*)} \tag{48}$$

Then, the estimate of the entire state $\chi_n$ can be expressed as, $$\hat{\chi}_n = \{\hat{\chi}_n^{P_1,(i_{1,n}^*)}, \hat{\chi}_n^{P_2,(i_{2,n}^*)}, \hat{\chi}_n^{K,(i_{MAP,n}^*)}\}. \tag{49}$$

---

Algorithm 2 Table - Dual MAM-PF Method Steps

Initialization for j = 1, 2 do for i = 1, ..., $N_p$ do

Sample $x_0^{P_j,(i)} \sim \pi_0(x_0^{P_j})$         $\hat{x}_{0:-1}^{K,(i)} = E[x_0^{K,(i)} | x_0^{P,(i)}]$         $\alpha_0^{(i)} = \pi_0(x_0^{P,(i)}) p(y_0 | x_0^{P,(i)}, x_0^{K,(i)})$ Algorithm 2 Table - Dual MAM-PF Method Steps $$z_0^{(i)} = x_0^{(i)}$$

end for $$i_{j,0}^* = \underset{i_j}{\operatorname{argmax}}\, \alpha_{j,o}^{(i,j)}$$

end for $$i_{MAP,0}^* = \underset{i_{j,0}^*}{\operatorname{argmax}}\, \alpha_{j,0}^{(i_{j,0}^*)}$$

$$\hat{x}_0 = \left\{ x_0^{P_1,(i_{1,0}^*)}, x_0^{P_2,(i_{2,0}^*)}, x_0^{K,(i_{MAP,0}^*)} \right\}$$

for $n = 1, \ldots, N_T$ do
  for $j = 1, 2$ do
    for $i_j = 1, \ldots, N_p$ do
    MAP Estimation $$x_n^{P_j,(i_j)} \sim q_n\!\left(x_n^{P_j,(i_j)} \,\Big|\, x_{n-1}^{P_j,(i_j)}, y_n\right)$$

$$k_j^* = \underset{k_j}{\operatorname{argmax}}\, \alpha_{j,n-1}^{(k_j)} p\!\left(x_{n-1}^{P_j,(i_j)} \,\Big|\, x_{n-1}^{P_j,(k_j)}\right)$$

Marginalized Sequential Estimation $$x_n^{P,(i_j)} = \left\{ x_n^{P_1,(i_{1,n-1}^*)}, \ldots, x_n^{P_j,(i_j)}, \ldots, x_n^{P_{N_j},(i_{N_j,n-1}^*)} \right\}$$

$$\hat{y}_{n|0:n-1} = H_n\!\left(x_n^{P,(i_j)}\right)\hat{x}_{n|0:n-1}^{K,(k_j^*)}$$

$$e_n = y_n - \hat{y}_{n|0:n-1}$$

$$R_{v,n} = \left[e_n e_n^T - H_n(x_n^{P,(i_j)}) C_{n|0:n-1}^{(k_j^*)} H_n(x_n^{P,(i_j)})^T\right]_+$$

$$\hat{R}_{v,n} = \beta \hat{R}_{v,n-1}^{(k_j^*)} + (1-\beta) R_{v,n}$$

$$R_{e,n} = H_n(x_n^{P,(i_j)}) C_{n|0:n-1}^{(k_j^*)} H_n(x_n^{P,(i_j)})^T + \hat{R}_{v,n}$$

$$K_n = C_{n|0:n-1}^{(k_j^*)} H_n(x_n^{P,(i_j)})^T (R_{e,n})^{-1}$$

$$\hat{x}_{n|0:n}^{K,i,j} = \hat{x}_{n|0:n-1}^{K,(k_j^*)} + K_n e_n$$

$$C_{n|0:n} = [I - K_n H_n(x_n^{P,(i_j)})] C_{n|0:n-1}^{(k_j^*)}$$

$$\hat{x}_{n+1|0:n}^{K,(i,j)} = F_n(x_n^{P,(i_j)}) \hat{x}_{n|0:n}^{K,i,j} \;\&\; \hat{R}_{v,n}^{(i,j)} = \hat{R}_{v,n}$$

$$C_{n+1|0:n}^{(i,j)} = F_n(x_n^{P,(i_j)}) C_{n|0:n} F_n(x_n^{P,(i_j)})^T + Q_u^K$$

$$\alpha_{j,n}^{(i,j)} = \alpha_{j,n-1}^{(k_j^*)} p\!\left(y_n \,\Big|\, x_n^{P,(i_j)}, \hat{x}_{n|0:n-1}^{K,(k_j^*)}\right)$$

$$p\!\left(x_n^{P_j,(i_j)} \,\Big|\, x_{n-1}^{P_j,(k_j^*)}\right)$$

end for
  Update MAP State Estimate $$i_{j,n}^* = \underset{i_j}{\operatorname{argmax}}\, \alpha_{j,n}^{(i,j)}$$

end for $$i_{MAP,n}^* = \underset{i_{j,n}^*}{\operatorname{argmax}}\, \alpha_{j,n}^{(i_{j,n}^*)}$$

$$\hat{x}_n = \left\{ \hat{x}_n^{P_1,(i_{1,n-1}^*)}, \hat{x}_n^{P_2,(i_{2,n}^*)}, \hat{x}_n^{K,(i_{MAP,n}^*)} \right\}$$

end for

H.4. ABP Signal Envelope Estimation

Given the estimated signal parameters in (26)-(34), according to one embodiment, it is possible to estimate the upper envelope ($e_{\mu,n}$) and lower envelope ($e_{l,n}$) of ABP signals by following steps below, $$\theta_{max,n}^c = \underset{\theta}{\operatorname{argmax}} \sum_{k=1}^{N_h^c} \rho_{k,n}[c_{1,k,n}\cos(k\theta) + c_{2,k,n}\sin(k\theta)]$$

$$\theta_{min,n}^c = \underset{\theta}{\operatorname{argmin}} \sum_{k=1}^{N_h^c} \rho_{k,n}[c_{1,k,n}\cos(k\theta) + c_{2,k,n}\sin(k\theta)]$$

$$\kappa_{max,k,n} = c_{1,k,n}\cos(k\theta_{max,n}^c) + c_{2,k,n}\sin(k\theta_{max,n}^c)$$

$$\kappa_{min,k,n} = c_{1,k,n}\cos(k\theta_{min,n}^c) + c_{2,k,n}\sin(k\theta_{min,n}^c)$$

$$e_{\mu,n} = \gamma_n + \sum_{k=1}^{N_h^c} \rho_{k,n} \kappa_{max,k,n} \qquad (50)$$

$$e_{l,n} = \gamma_n + \sum_{k=1}^{N_h^c} \rho_{k,n} \kappa_{min,k,n} \qquad (51)$$

where $\arg\max_\chi f(\chi)$ and $\arg\min_\chi f(\chi)$ are operators to obtain the value of $\chi$ for which $f(\chi)$ attains its maximum and minimum values, respectively.

H.5. Pulse Pressure Signal Envelope Estimation

The pulse pressure (PP) signal is the difference between the upper envelope $e_{\mu,n}$ and lower envelope $e_{l,n}$ of the ABP signal. This PP signal oscillates roughly at the respiratory rate. This oscillation is due to the respiratory effect on the variation of systemic ABP under full ventilation support. Within each respiratory cycle PP reaches its maximum ($PP_{max}$) and minimum ($PP_{min}$) values, which are two critical parameters to compute the PPV index. Traditionally, the $PP_{max}$ and $PP_{min}$ values have been computed only once per each respiratory cycle. Given the estimated signal parameters in (26)-(34), however, the continuous equivalents of $PP_{max}$ and $PP_{min}$ can be computed. They are the upper $\epsilon_{\mu,n}$ and lower $\epsilon_{l,n}$ envelopes of the PP signal. The upper envelope $\epsilon_{\mu,n}$ is the continuous estimate of $PP_{max}$ and the lower envelope $\epsilon_{l,n}$ that of $PP_{min}$. The $\epsilon_{\mu,n}$ and $\epsilon_{l,n}$ values can be estimated as described below, $$\varrho_{k,n} = \sum_{j=1}^{N_h^r} m_{1,k,j,n}\cos(j\theta) + m_{2,k,j,n}\sin(j\theta)$$

$$\theta_{max,n}^r = \underset{\theta}{\operatorname{argmax}} \sum_{k=1}^{N_h^c} (1+\varrho_{k,n})(\kappa_{max,k,n} - \kappa_{min,k,n})$$

$$\theta_{min,n}^r = \underset{\theta}{\operatorname{argmin}} \sum_{k=1}^{N_h^c} (1+\varrho_{k,n})(\kappa_{max,k,n} - \kappa_{min,k,n})$$

$$\varrho_{max,k,n} = \sum_{j=1}^{N_h^r} m_{1,k,j,n}\cos(j\theta_{max,n}^r) + m_{2,k,j,n}\sin(j\theta_{max,n}^r)$$

$$\varrho_{min,k,n} = \sum_{j=1}^{N_h^r} m_{1,k,j,n}\cos(j\theta_{min,n}^r) + m_{2,k,j,n}\sin(j\theta_{min,n}^r)$$

$$\varepsilon_{\mu,n} = \sum_{k=1}^{N_h^c} (1 + \varrho_{max,k,n})(\kappa_{max,k,n} - \kappa_{min,k,n}) \quad (52)$$

$$\varepsilon_{l,n} = \sum_{k=1}^{N_h^c} (1 + \varrho_{min,k,n})(\kappa_{max,k,n} - \kappa_{min,k,n}) \quad (53)$$

where $1+\varrho_{k,n}$ is equal to $\rho_{k,n}$, and $\epsilon_{\mu,n}$ and $\epsilon_{l,n}$ are the continuous estimates of the $PP_{max}$ and $PP_{min}$, respectively.

H.6. Pulse Pressure Variation Calculation

Given the $\epsilon_{\mu,n}$ and lower $\epsilon_{l,n}$ values, it is possible to calculate the PPV index. According to one embodiment, it can be computed as follows, $$PPV(\%) = 100 \times \frac{\varepsilon_{max} - \varepsilon_{min}}{(\varepsilon_{max} + \varepsilon_{min})/2} \quad (54)$$

This new PPV index is different from the traditional PPV index described in (1) because the new one is continuous in time while the traditional one can be obtained only once per each respiratory cycle.

While particular embodiments have been described, it is understood that, after learning the teachings contained in this disclosure, modifications and generalizations will be apparent to those skilled in the art without departing from the spirit of the disclosed embodiments. It is noted that the foregoing embodiments and examples have been provided merely for the purpose of explanation and are in no way to be construed as limiting. While the apparatus has been described with reference to various embodiments, it is understood that the words which have been used herein are words of description and illustration, rather than words of limitation. Further, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. A method for assessing fluid responsiveness comprising:
   (a) obtaining a cardiovascular signal; and
   (b) computing a dynamic index predictive of fluid responsiveness from said cardiovascular signal using a hardware device with one or more processors configured for implementing a nonlinear state space estimator, said nonlinear state space estimator comprising a state space model wherein a plurality of cardiac harmonics are separately modulated by respiratory fluctuations;
   whereby said dynamic index predictive of fluid responsiveness enables a practitioner to assess fluid responsiveness and guide fluid therapy.

2. The method of claim 1, wherein said cardiovascular signal is an arterial blood pressure signal.

3. The method of claim 1, wherein said cardiovascular signal is a plethysmographic signal.

4. The method of claim 1, wherein said dynamic index predictive of fluid responsiveness is a nonlinear function of said cardiovascular signal.

5. The method of claim 4, wherein said dynamic index predictive of fluid responsiveness is substantially equivalent to a variation in pulse pressure of said cardiovascular signal due to respiration.

6. The method of claim 5, wherein said nonlinear state space estimator is based on a nonlinear state space model of cardiovascular signals.

7. The method of claim 6, wherein said nonlinear state space estimator is a computational Bayesian estimator.

8. The method of claim 7, wherein said computational Bayesian estimator is a sequential Monte Carlo estimator.

9. The method of claim 8, wherein said sequential Monte Carlo estimator is a marginalized particle filter.

10. The method of claim 9, wherein said marginalized particle filter is an a-posteriori adaptive marginalized particle filter.

11. An apparatus for assessing fluid responsiveness, comprising:
    (a) a measuring unit for measuring a cardiovascular signal; and
    (b) a processor configured for computing a dynamic index predictive of fluid responsiveness from said cardiovascular signal using a nonlinear state space estimator, said state space estimator comprising a state space model wherein a plurality of cardiac harmonics are separately modulated by respiratory fluctuations;
    whereby said dynamic index predictive of fluid responsiveness enables a practitioner to assess fluid responsiveness and guide fluid therapy.

12. The apparatus of claim 11, wherein said dynamic index predictive of fluid responsiveness is substantially equivalent to a variation in pulse pressure of said cardiovascular signal due to respiration.

13. The apparatus of claim 12, wherein said nonlinear state space estimator is based on a nonlinear state space model of said cardiovascular signal.

14. The apparatus of claim 13, wherein said nonlinear state space estimator is a computational Bayesian estimator.

15. The apparatus of claim 14, wherein said computational Bayesian estimator is a sequential Monte Carlo estimator.

16. The apparatus of claim 15, wherein said sequential Monte Carlo estimator is a marginalized particle filter.

17. The apparatus of claim 16, wherein said marginalized particle filter is an a-posteriori adaptive marginalized particle filter.

18. The apparatus of claim 17, wherein said marginalized particle filter is adapted to work on a cardiovascular signal from a spontaneously breathing patient.

* * * * *